(12) United States Patent
Yamada

(10) Patent No.: US 11,229,346 B2
(45) Date of Patent: Jan. 25, 2022

(54) MEDICAL METHOD FOR A LUMEN

(71) Applicant: OLYMPUS CORPORATION, Tokyo (JP)

(72) Inventor: Tetsuhiro Yamada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 742 days.

(21) Appl. No.: 16/191,714

(22) Filed: Nov. 15, 2018

(65) Prior Publication Data
US 2020/0154983 A1 May 21, 2020

(51) Int. Cl.
*A61B 1/00* (2006.01)
*A61B 1/01* (2006.01)
*A61M 25/06* (2006.01)
*A61M 25/02* (2006.01)

(52) U.S. Cl.
CPC ........... *A61B 1/00154* (2013.01); *A61B 1/01* (2013.01); *A61M 25/0662* (2013.01); *A61M 2025/0293* (2013.01)

(58) Field of Classification Search
None
See application file for complete search history.

(56) References Cited

U.S. PATENT DOCUMENTS

| | | | | |
|---|---|---|---|---|
| 5,645,519 A * | 7/1997 | Lee | ....................... | A61B 1/2676 600/114 |
| 6,585,639 B1 * | 7/2003 | Kotmel | .............. | A61B 1/00082 600/114 |
| 2007/0055101 A1 * | 3/2007 | Yoshida | ............. | A61B 1/00135 600/116 |
| 2008/0033244 A1 | 2/2008 | Matsui et al. | | |
| 2013/0053636 A1 * | 2/2013 | Hayman | ........... | A61M 16/0459 600/104 |
| 2016/0158047 A1 * | 6/2016 | Treacy | .................... | A61F 2/966 623/23.7 |

FOREIGN PATENT DOCUMENTS

| | | |
|---|---|---|
| EP | 1 884 186 A1 | 2/2008 |
| JP | 2008-035909 A | 2/2008 |
| JP | 2013-085812 A1 | 5/2013 |

* cited by examiner

*Primary Examiner* — Timothy J Neal
(74) *Attorney, Agent, or Firm* — Scully, Scott, Murphy & Presser, P.C.

(57) ABSTRACT

A medical method for a lumen of a body includes, introducing a first endoscope and a first overtube up to a strictured area inside the lumen, the first overtube having a first channel having an inner diameter such that the first endoscope can be introduced into the lumen, introducing a second overtube into the lumen by using the first overtube as a guide, the second overtube having a second channel having an inner diameter larger than an outer diameter of the first overtube such that a second endoscope can be introduced into the lumen, the second endoscope having an outer diameter larger than an outer diameter of the first endoscope, removing the first endoscope and the first overtube from an interior of the second channel, inserting the second endoscope into the lumen by using the second channel as a guide, and dilating the strictured area by using the second endoscope.

5 Claims, 11 Drawing Sheets

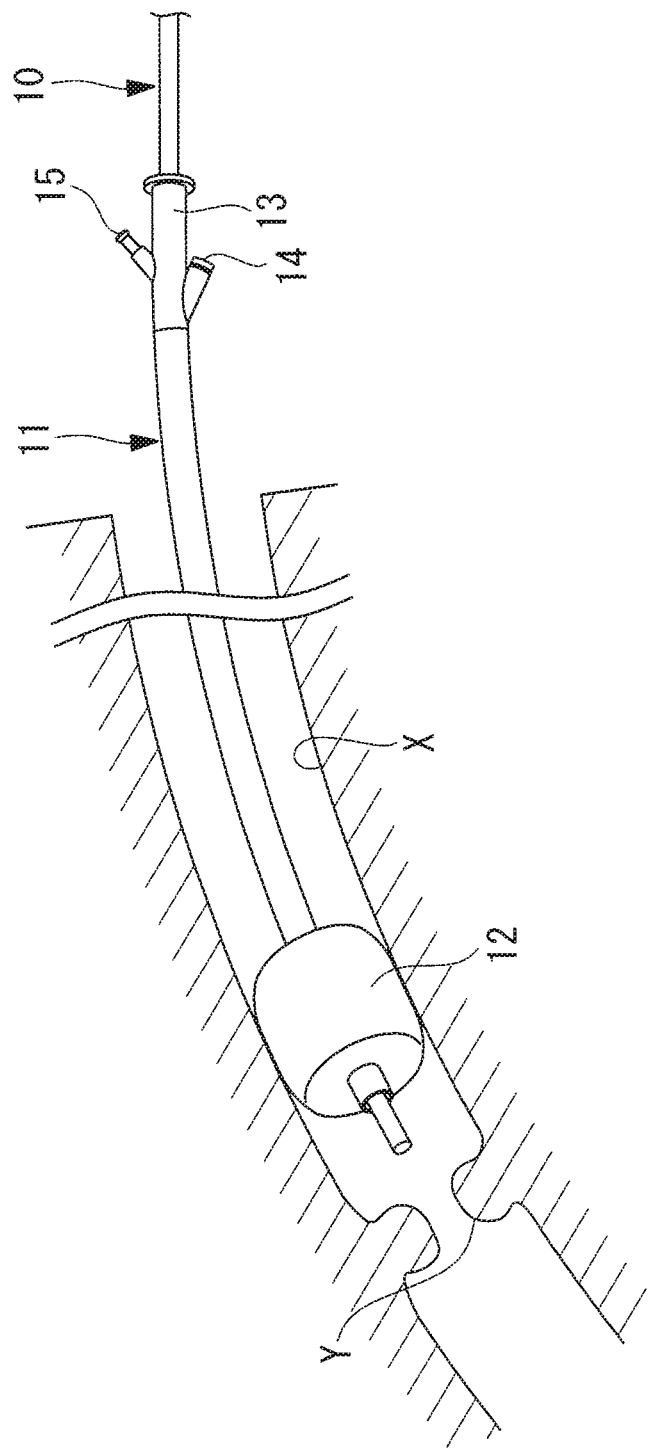

MEDICAL METHOD FOR A LUMEN

TECHNICAL FIELD

The present invention relates to a medical method for a lumen.

BACKGROUND ART

When deep imaging is conducted by inserting a small-diameter overtube into a lumen and observing a portion deeper than a strictured area inside the lumen by using a small-diameter endoscope inserted into the overtube and when it is determined from the results that stricture dilation can be carried out without any problem, the endoscope must be replaced with a large-diameter endoscope having a channel through which a dilation treatment tool to be inserted to the strictured area can be supplied.

Conversely, when a large-diameter overtube is inserted into a lumen and the strictured area inside the lumen is observed with a large-diameter endoscope inserted into the overtube and when it is determined from the results that there is a need for deep imaging of the portion deeper than the strictured area, the endoscope must be replaced with a small-diameter endoscope that can pass through the strictured area and conduct deep imaging.

In order to replace a small-diameter overtube and a small-diameter endoscope with a large-diameter overtube and a large-diameter endoscope, the small-diameter overtube and the small-diameter endoscope must both be removed, and the large-diameter overtube and the large-diameter endoscope must again be inserted. Likewise, in order to replace a large-diameter overtube and a large-diameter endoscope with a small-diameter overtube and a small-diameter endoscope, the large-diameter overtube and the large-diameter endoscope must both be removed, and the small-diameter overtube and small small-diameter endoscope must again be inserted.

In these cases, a long time is needed for the operation of inserting a new overtube.

CITATION LIST

Patent Literature

{PTL 1} None

SUMMARY OF INVENTION

According to one aspect of the present invention, there is provided a medical method for a lumen of a human body, the method comprising: introducing a first endoscope and a first overtube up to a strictured area inside the lumen, the first overtube having a first channel having an inner diameter such that the first endoscope can be introduced into the lumen; introducing a second overtube into the lumen by using the first overtube as a guide, the second overtube having a second channel having an inner diameter larger than an outer diameter of the first overtube such that a second endoscope can be introduced into the lumen, the second endoscope having an outer diameter larger than an outer diameter of the first endoscope; removing the first endoscope and the first overtube from an interior of the second channel; inserting the second endoscope into the lumen by using the second channel as a guide; and dilating the strictured area by using the second endoscope.

BRIEF DESCRIPTION OF DRAWINGS

FIG. 8 is a diagram illustrating a state in which the first endoscope and the first overtube are inserted into the lumen according to the medical method for a lumen illustrated in FIG. 1.

DESCRIPTION OF EMBODIMENTS

A medical method for a lumen according to one embodiment of the present invention will now be described with reference to the drawings.

The medical method for a lumen according to this embodiment is a method for dilating a strictured area formed in a lumen.

In order to dilate a strictured area (refer to FIG. 8) Y in a lumen (refer to FIG. 8) X, deep imaging must be performed to find whether a lesion, such as a longitudinal ulcer or a lesion with a cobblestone appearance, exists in a portion deeper than the strictured area Y so as ascertain that such a lesion does not exist and stricture dilation can be performed without any problem. In other words, in this case, a small-diameter first endoscope 10 is first introduced into the lumen past the strictured area Y so as to perform deep imaging in the deeper portion. If there is no problem, a second endoscope 20 having a diameter larger than the first endoscope 10 is introduced into the lumen X so as to replace the first endoscope 10, and a dilation tool, such as a balloon or a stent, is inserted into the strictured area Y via a channel in the second endoscope 20 so as to perform dilation.

Figure 1:
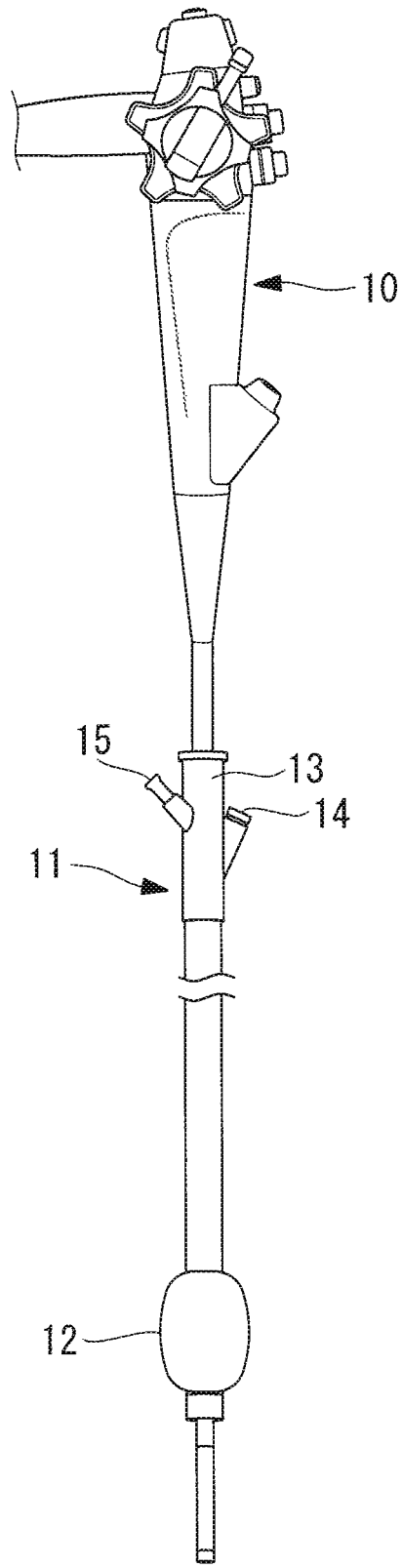
FIG. 1 is a front view illustrating a first endoscope and a first overtube used in a medical method for a lumen according to one embodiment of the present invention.
Figure 2:
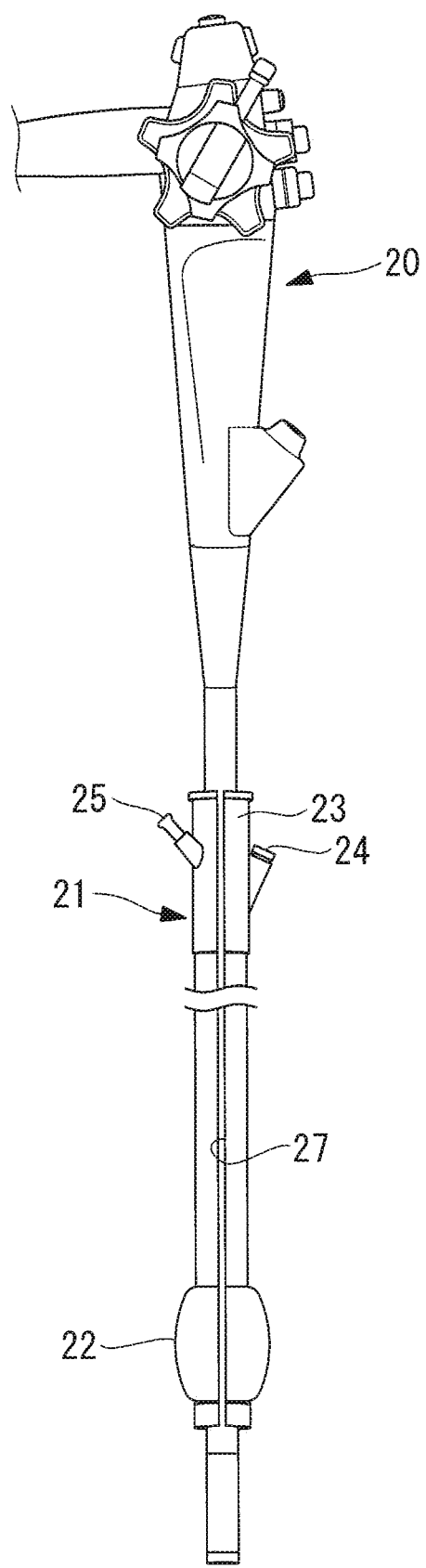
FIG. 2 is a front view illustrating a second endoscope and a second overtube used in the medical method for a lumen illustrated in FIG. 1.

In this case, the medical method for the lumen X according to this embodiment uses the small-diameter first endoscope 10 and a small-diameter first overtube 11 illustrated in FIG. 1 and the large-diameter second endoscope 20 and a large-diameter second overtube 21 illustrated in FIG. 2.

The first overtube 11 and the second overtube 21 are respectively equipped with inflatable and deflatable balloons 12 and 22 on the distal end side, and grip units 13 and 23 on the proximal end side, the grip units 13 and 23 respectively having balloon air valves 14 and 24 and water valves 15 and 25.

Figure 3:
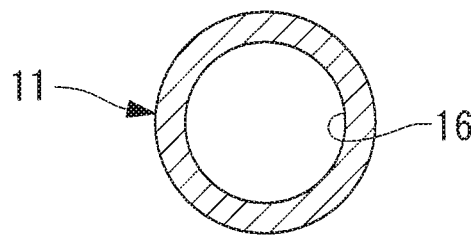
FIG. 3 is a cross-sectional view of the first overtube illustrated in FIG. 1.

As illustrated in FIG. 3, the first overtube 11 has a closed ring-shaped cross-sectional shape throughout the entire length in the length direction. The inner diameter of a first channel 16 of the first overtube 11 has a dimension with which the first endoscope 10 can be inserted thereinto with a space in the radial direction.

Figure 4:
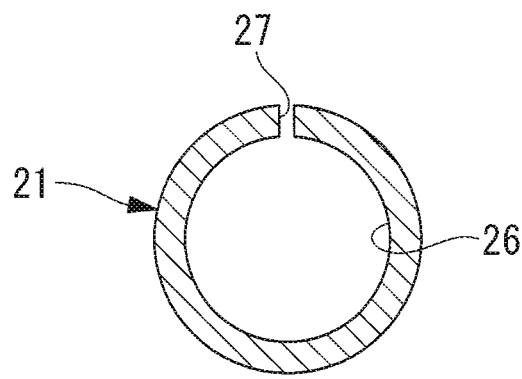
FIG. 4 is a cross-sectional view of the second overtube illustrated in FIG. 2.

Meanwhile, as illustrated in FIG. 4, the second overtube 21 has a letter C cross-sectional shape, which is formed by cutting a slit 27, throughout the entire length in the length direction. As illustrated in FIG. 4, the second overtube 21 in an empty state has the slit 27 that is narrowed, and the inner diameter of a second channel 26 of the second overtube 21 in that state is slightly smaller than the outer diameter of the first overtube 11.

Figure 5:
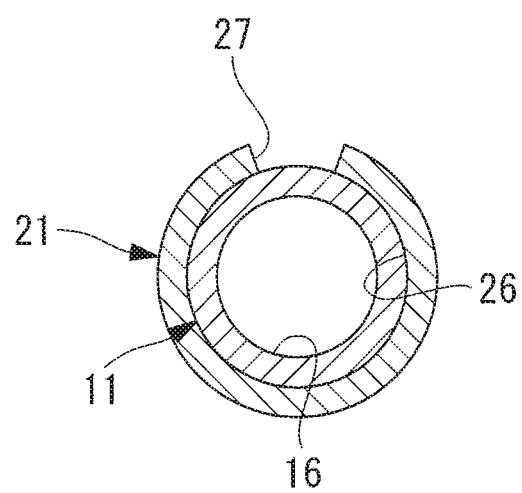
FIG. 5 is a cross-sectional view of a state in which the first overtube illustrated in FIG. 1 is covered with the second overtube illustrated in FIG. 2.

As illustrated in FIG. 5, when the first overtube 11 is inserted into the second channel 26 in the second overtube 21, the slit 27 opens, the inner diameter of the second overtube 21 is increased, and the inner surface of the second overtube 21 contacts the outer surface of the first overtube 11.

Figure 6:
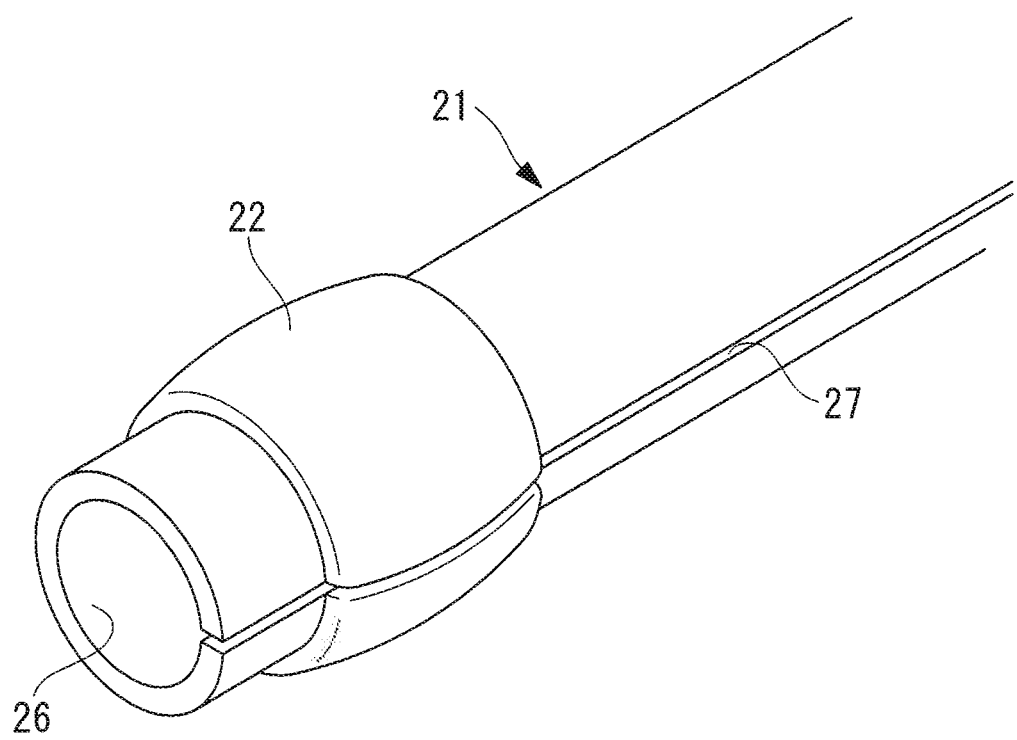
FIG. 6 is a perspective view of a balloon at a distal end of the second overtube illustrated in FIG. 2.

As illustrated in FIG. 6, the balloon 22 of the second overtube 21 has a letter C cross-sectional shape due to the presence of the slit 27.

Figure 7A:
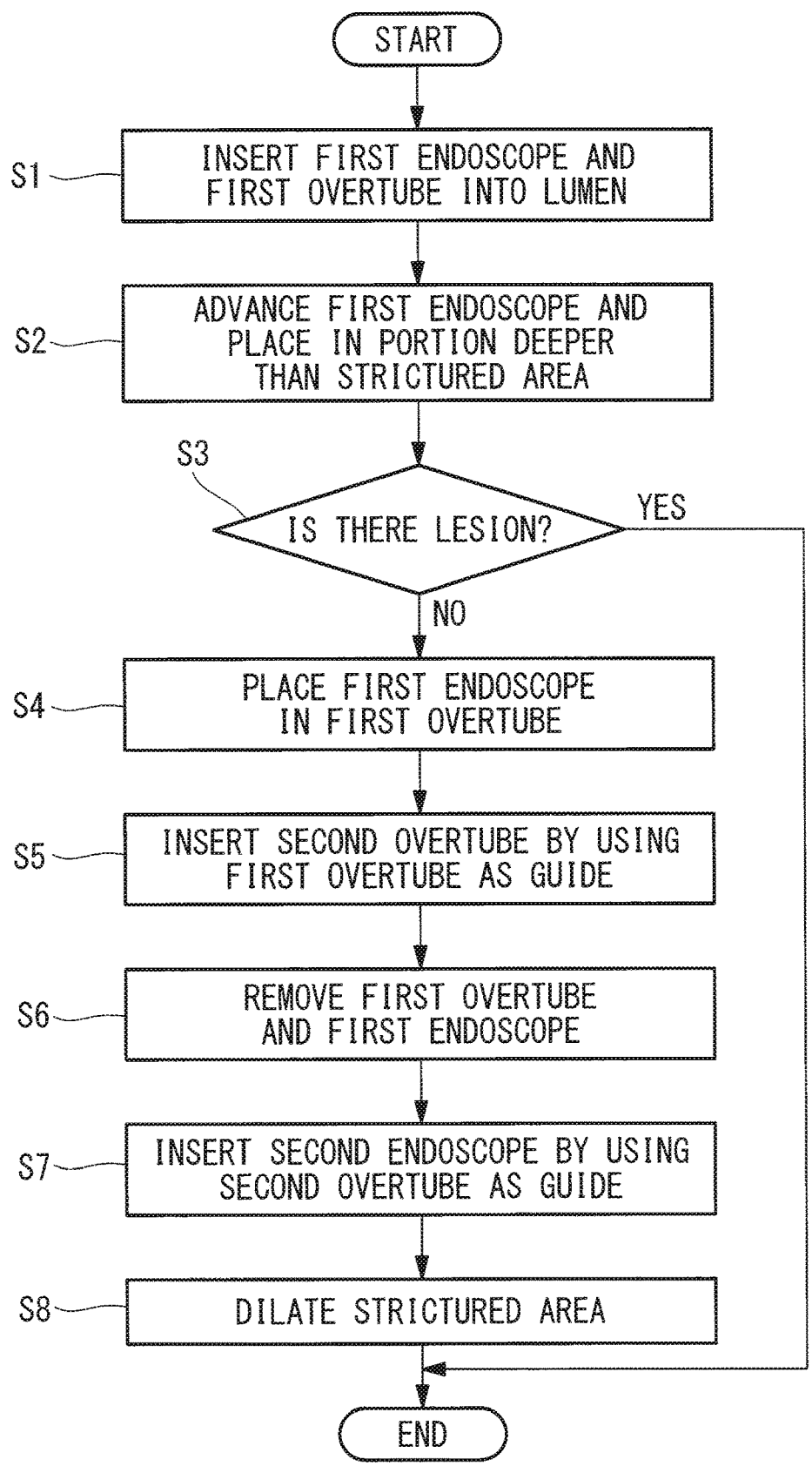
FIG. 7A is a flowchart illustrating the medical method for a lumen illustrated in FIG. 1.

As illustrated in FIGS. 7A and 8, in the medical method for the lumen X according to this embodiment, the first overtube 11 containing the first endoscope 10 is inserted into the lumen X (step S1).

The operation of inserting the first overtube 11 into the lumen X involves pressing the first overtube 11 forward in the length direction while checking the endoscope image acquired with the first endoscope 10 so as to advance the distal end position of the first overtube 11 in the lumen X. Subsequently, the balloon 12 at the distal end portion is inflated to fix the distal end portion of the first overtube 11 to the lumen X, and the first overtube 11 is pulled toward the proximal end side to pull back the lumen X toward the proximal end side.

Then, the operation of deflating the balloon 12, advancing the first overtube 11, inflating the balloon 12, and retracting the first overtube 11 is repeated so that the first overtube 11 can be gradually advanced with respect to the lumen X and the first overtube 11 can be inserted up to a portion at the front of the strictured area Y.

When the strictured area Y appears in the endoscope image, the balloon 12 of the first overtube 11 is inflated to fix the first overtube 11 to the lumen X, and the first endoscope 10 is caused to protrude from the distal end of the first overtube 11 by using the first overtube 11 as a guide (step S2).

Figure 9:
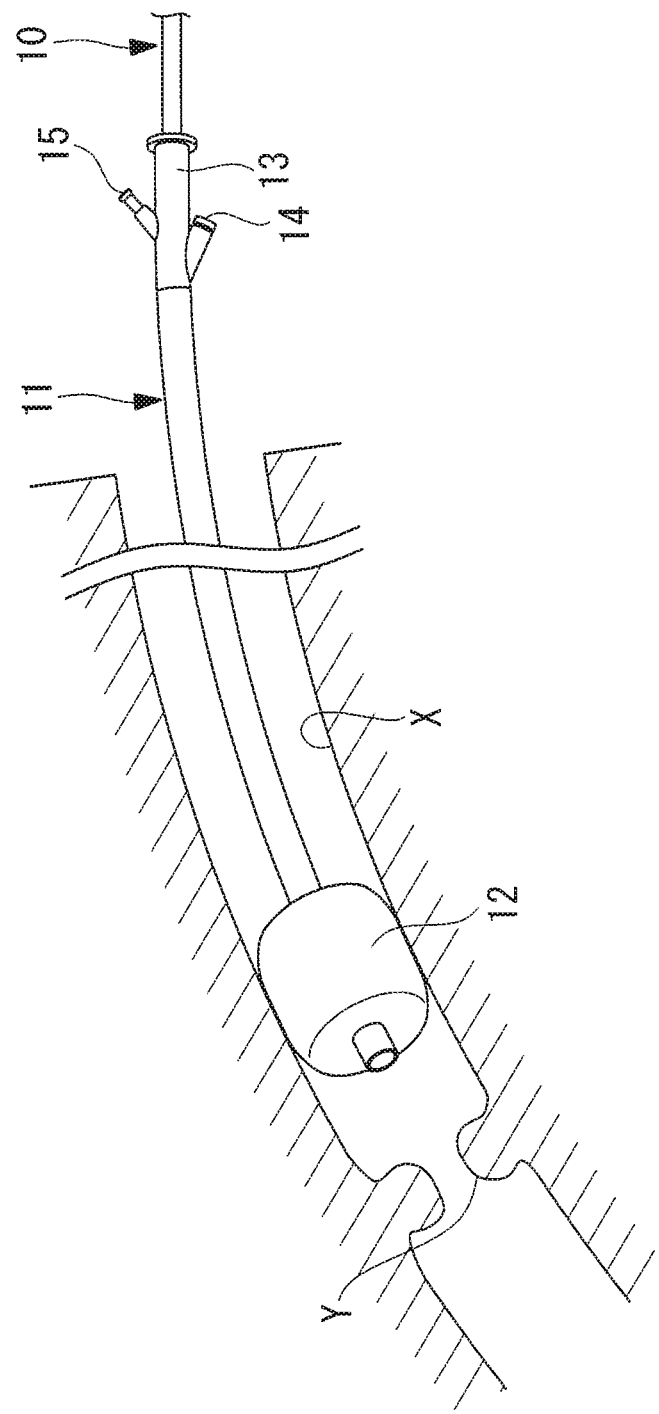
FIG. 9 is a diagram illustrating a state in which the first endoscope illustrated in FIG. 8 is advanced so that the second overtube covers the outer side of the first overtube containing the first endoscope observing a portion deeper than a strictured area.

In this state, from the image taken with the first endoscope 10, whether a lesion, bleeding, or the like is present around the strictured area Y is checked (step S3). This is to judge whether or not the strictured area Y dilation procedure can be performed. If it is judged that the strictured area Y dilation procedure can be performed, as illustrated in FIG. 9, the first endoscope 10 is retracted and housed inside the first overtube 11 (step S4).

Figure 10:
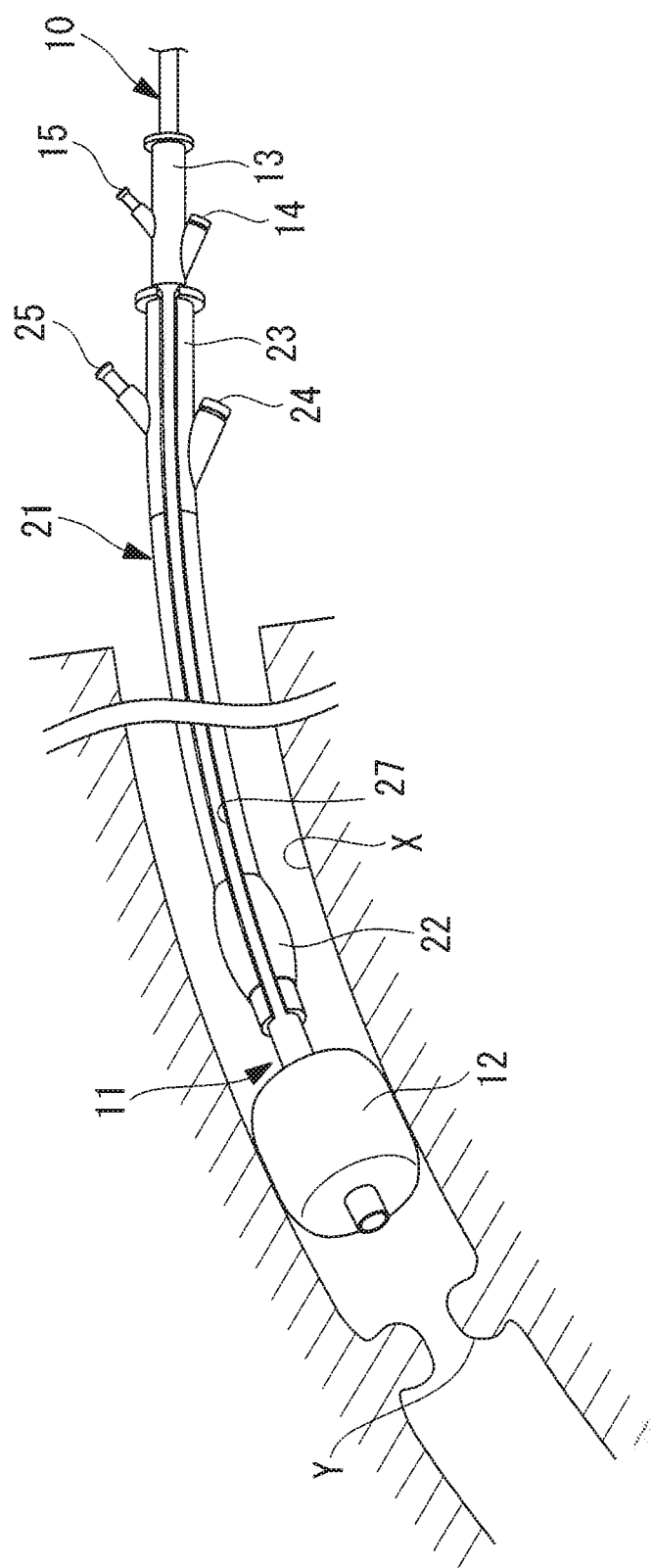
FIG. 10 is a diagram illustrating a state in which the second overtube is inserted into the lumen by using the first overtube as a guide.

Next, the slit 27 of the second overtube 21 is widened, the outer side of the first overtube 11 is covered with the second overtube 21, and, as illustrated in FIG. 10, the second overtube 21 is inserted into the lumen X by using the first overtube 11 as a guide (step S5).

In order to cover the outer side of the first overtube 11, which is inserted into the lumen X, with the second overtube 21, it is necessary to start covering the first overtube 11 from the proximal end side exposed outside the body. Since the proximal end side of the first overtube 11 has the balloon air valve 14 and the water valve 15 in the grip unit 13 and has a large diameter, the slit 27 of the second overtube 21 is widened so as to cover the outer surface of the first overtube 11 on the distal end side of the grip unit 13 of the first overtube 11 with the second overtube 21.

The second overtube 21 thereon is then advanced with respect to the first overtube 11. Since the inner diameter of the second overtube 21 is slightly smaller than the outer diameter of the first overtube 11, the second overtube 21 is advanced while the slit 27 is slightly widened and the inner surface is in contact with the outer surface of the first overtube 11 as the second overtube 21 covers the first overtube 11. As a result, the second overtube 21 is inserted into the lumen X by using the first overtube 11 as a guide.

Figure 11:
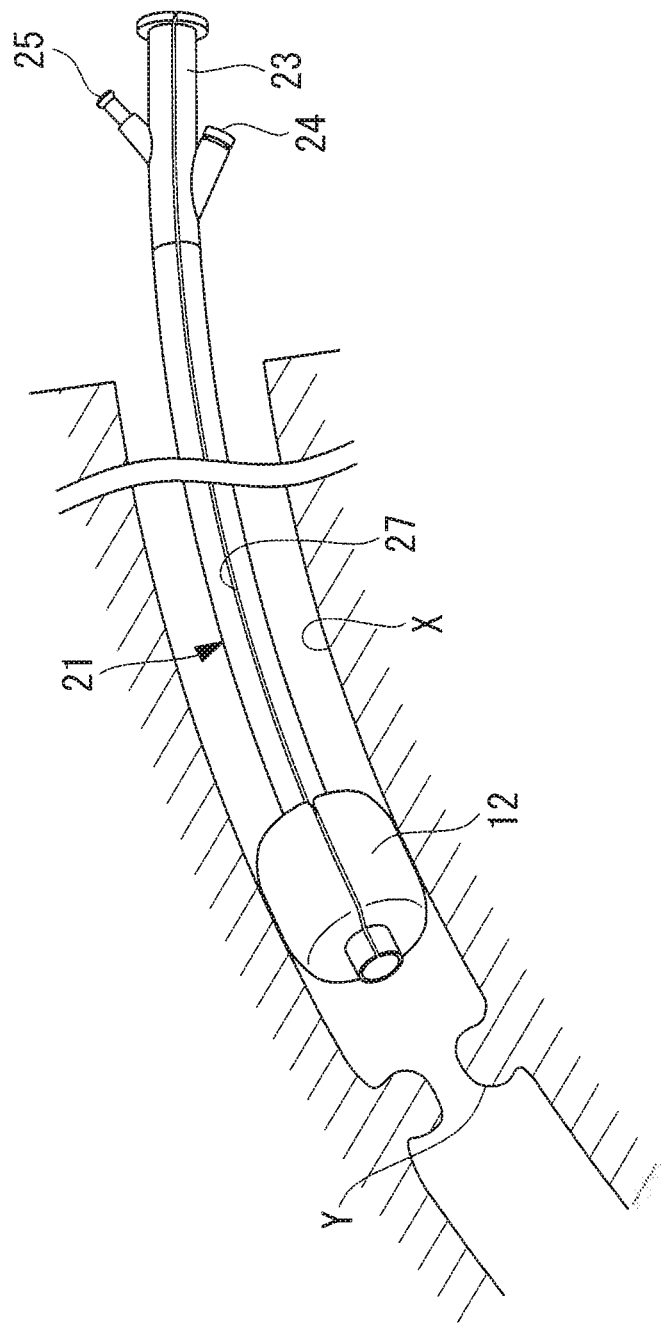
FIG. 11 is a diagram illustrating a state in which the first endoscope and the first overtube are removed from the interior of the second overtube illustrated in FIG. 10.

After the distal end of the second overtube 21 reaches the same position as the distal end of the first overtube 11, the first overtube 11 and the first endoscope 10 are removed from the interior of the second overtube 21 (step S6). As a result, as illustrated in FIG. 11, only the second overtube 21 remains inside the lumen X.

In this state, the second endoscope 20 is inserted into the second overtube 21 by using the second overtube 21 as a guide (step S7). Since the second endoscope 20 has a larger outer diameter than the first endoscope 10, a large channel can be formed, and a dilation tool is introduced through the channel to dilate the strictured area Y with a dilation tool (step S8). Alternatively, the strictured area Y may be dilated by inserting the second endoscope 20 or the second overtube 21 so as to force the strictured area Y open.

As described above, according to the medical method for the lumen X of this embodiment, there is no need to repeat the insertion operation of inserting the first overtube 11 when the large-diameter second overtube 21 is introduced to replace the small-diameter first overtube 11. The first overtube 11 insertion operation takes a long time since it involves, as described above, deflation of the balloon 12, advancement of the first overtube 11, inflation of the balloon 12, and pulling of the lumen X.

When inserting the second overtube 21, since there is no need to repeat the first overtube 11 insertion operation, there is an advantage in that the workload of the user can be reduced. In other words, there is an advantage in that the time required to replace the small-diameter first overtube 11 and the first endoscope 10 inserted into the lumen X with the large-diameter second endoscope 20 can be shortened.

Figure 7B:
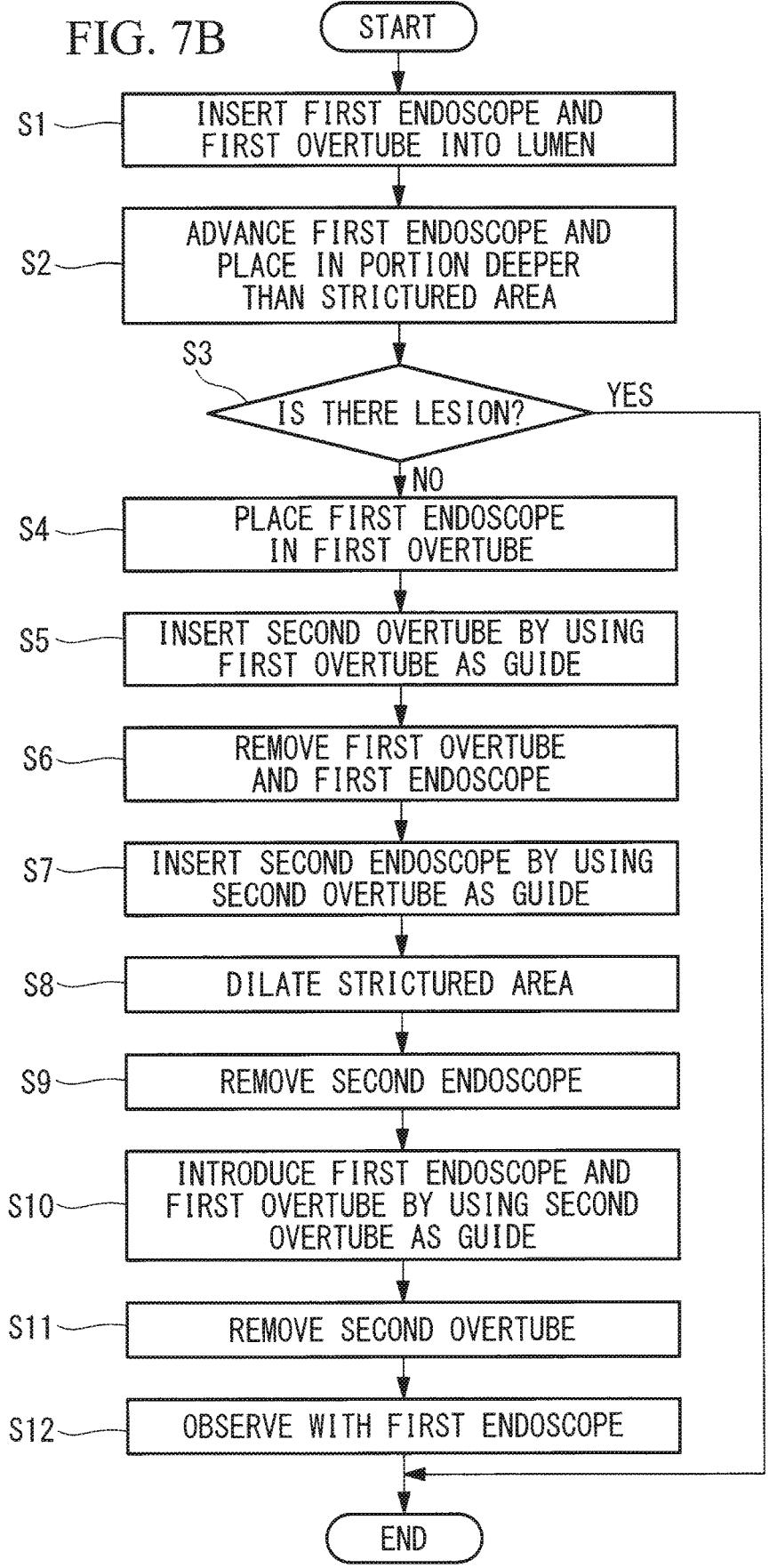
FIG. 7B is a flowchart illustrating a modification of the medical method for a lumen illustrated in FIG. 7A.

In this embodiment, after the strictured area Y is dilated, the first endoscope 10 and the first overtube 11 may be placed instead so that treatment and imaging in a region deeper than the strictured area Y can be carried out. Specifically, as illustrated in FIG. 7B, the second endoscope 20 is removed from the second overtube 21 (step S9). Then, the first endoscope 10 and the first overtube 11 are inserted by using the second overtube 21 as a guide (step S10), and, after the insertion, the second overtube 21 is removed from the interior of the lumen X (step S11). The interior of the lumen X is observed with the first endoscope 10 inserted up to a portion deeper than the strictured area Y (step S12). There is an advantage in that since the second endoscope 20 can be replaced with the first endoscope 10 while maintaining the insertion position in the lumen X, the time required for the replacement can be shortened.

Next, a medical method for a lumen X according to one embodiment of the present invention is described with reference to the drawings.

The medical method for a lumen X according to this embodiment is a method for observing a portion deeper than the strictured area Y formed in a lumen X.

When dilating the strictured area Y in the lumen X, it is necessary to insert the large-diameter second endoscope 20 having a channel into which a dilation tool can be inserted into the lumen X. However, after inserting the large-diameter second endoscope 20 up to a portion in front of the strictured area Y, there is a possibility that a lesion may exist in a portion deeper than the strictured area Y and it is necessary to confirm whether the stricture dilation can be carried out without any problem.

In such a case, the large-diameter second endoscope 20 must be temporarily removed, and the small-diameter first endoscope 10 must be introduced into the lumen X and advanced past the strictured area Y so as to perform deep imaging in the deeper area.

Figure 12:
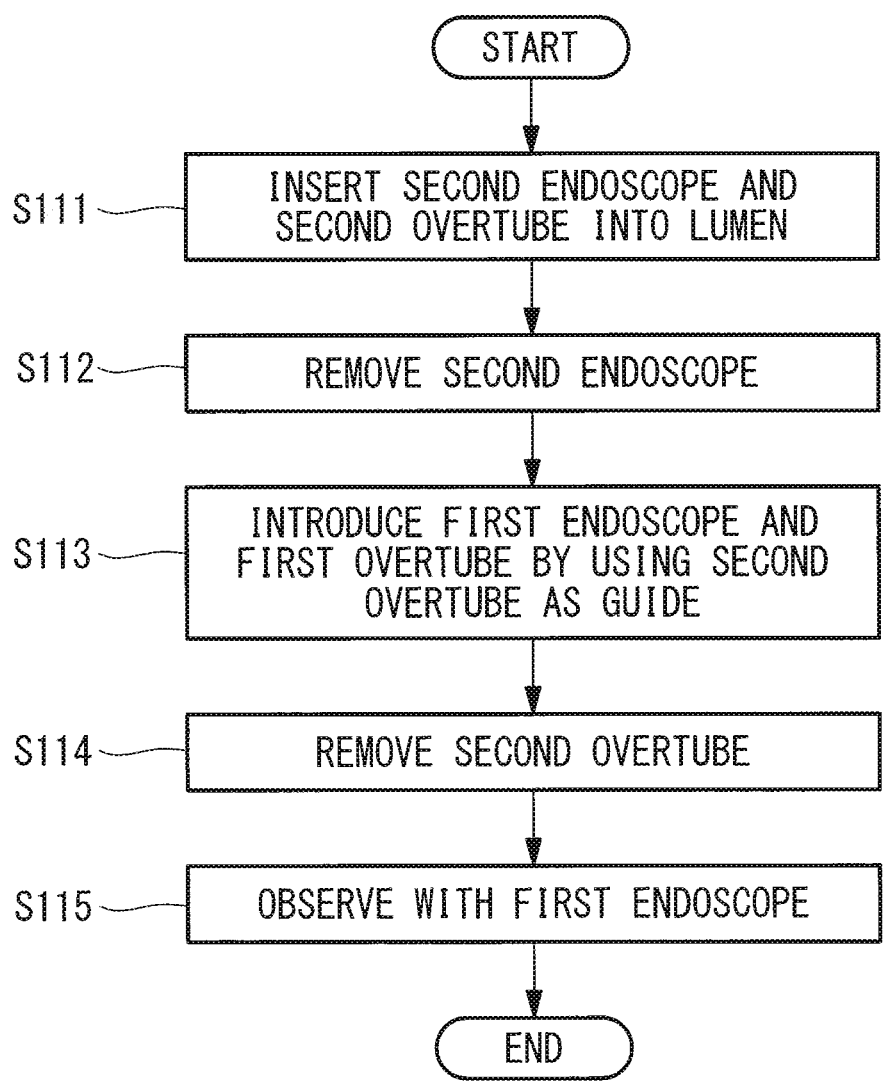
FIG. 12 is a flowchart illustrating a medical method for a lumen according to one embodiment of the present invention.

As illustrated in FIG. 12, in the medical method for the lumen X according to this embodiment, the second overtube 21 containing the second endoscope 20 is introduced up to the strictured area Y in the lumen X (step S111).

Next, the second endoscope 20 is removed from the second channel 26 of the second overtube 21 (step S112), and the first endoscope 10 and the first overtube 11 are introduced into the lumen X by using the second channel 26 of the second overtube 21 as a guide (step S113).

Then, the second overtube 21 is removed from the interior of the lumen X (step S114), and the first endoscope 10 is inserted up to a portion deeper than the strictured area Y to carry out imaging (step S115).

As described above, according to the medical method for the lumen X of this embodiment, when the small-diameter first overtube 11 is introduced to replace the large-diameter second overtube 21, there is no need to repeat the insertion operation of inserting the second overtube 21. The second overtube 21 insertion operation takes a long time since it involves deflation of the balloon 22, advancement of the second overtube 21, inflation of the balloon 22, and pulling of the lumen X.

When inserting the first overtube 11, since there is no need to repeat the second overtube 21 insertion operation, there is an advantage in that the workload of the user can be reduced. In other words, there is an advantage in that the time required to replace the large-diameter second overtube 21 and the second endoscope 20 inserted into the lumen X with the small-diameter first endoscope 10 can be shortened.

The aforementioned embodiments are derived from the following aspects of the present invention.

According to one aspect of the present invention, there is provided a medical method for a lumen of a human body, the method comprising: introducing a first endoscope and a first overtube up to a strictured area inside the lumen, the first overtube having a first channel having an inner diameter such that the first endoscope can be introduced into the lumen; introducing a second overtube into the lumen by using the first overtube as a guide, the second overtube having a second channel having an inner diameter larger than an outer diameter of the first overtube such that a second endoscope can be introduced into the lumen, the second endoscope having an outer diameter larger than an outer diameter of the first endoscope; removing the first endoscope and the first overtube from an interior of the second channel; inserting the second endoscope into the lumen by using the second channel as a guide; and dilating the strictured area by using the second endoscope.

According to this aspect, when switching from a state in which the first overtube and the first endoscope are introduced up to the strictured area inside the lumen to a state in which the second overtube and the second endoscope are introduced up to the strictured area inside the lumen, the second overtube is introduced on the outer side of the first overtube by using the already introduced first overtube as a guide. Then the first overtube and the first endoscope are removed from the interior of the second overtube, and, lastly, the second endoscope is inserted by using the second channel as a guide. In this manner, compared to the case in which the first overtube and the first endoscope are removed from the interior of the lumen and then the second overtube is introduced into the empty lumen, there is no need to perform a new re-insertion operation, the operation time can be significantly reduced, and the load on the patient can be reduced.

In the aspect described above, the second overtube may have an openable and closable slit that extends throughout the entire length at one portion in a circumferential direction, and the second overtube may be introduced into the lumen by using the first overtube as a guide while the slit is opened and the first overtube is inserted into the second channel in the second overtube.

According to this feature, even when a large-diameter portion exists on the proximal end side of the first overtube, the second overtube can be positioned so that the second overtube starts to cover the first overtube from a vicinity of the proximal end of the first overtube, and the first overtube can be inserted into the second channel of the second overtube. That is, the second overtube can be easily inserted into the lumen by using the first overtube as a guide while having the first overtube inserted in the lumen.

In the aspect described above, the method may further include removing the second endoscope from an interior of the second channel; introducing the first endoscope and the first overtube into the lumen by using the second channel as a guide; removing the second overtube from an interior of the lumen; and carrying out observation by inserting the first endoscope to a position deeper than the dilated strictured area.

According to another aspect of the present invention, there is provided a medical method for a lumen of a human body, the method comprising: introducing a second endoscope and a second overtube up to a strictured area inside the lumen, the second overtube having a second channel having an inner diameter such that the second endoscope can be introduced into the lumen; removing the second endoscope from an interior of the second channel; introducing a first endoscope and a first overtube into the lumen by using the second channel as a guide, the first overtube having a first channel having an inner diameter such that the first endoscope can be introduced into the lumen; removing the second overtube from an interior of the lumen; and carrying out observation by inserting the first endoscope up to a position deeper than the strictured area.

According to this aspect, when switching from a state in which the second overtube and the second endoscope are introduced up to the strictured area inside the lumen to a state in which the first overtube and the first endoscope are introduced up to the strictured area inside the lumen, the second endoscope is removed from the interior of the second channel of the already introduced second overtube, the first endoscope and the first overtube are introduced into the lumen by using the second channel as a guide, and the second overtube is removed from the interior of the lumen. In this manner, compared to the case in which the first overtube is introduced into an empty lumen, there is no need to perform a new re-insertion operation, the operation time can be significantly reduced, and the load on the patient can be reduced.

In the aspect described above, the second overtube may have an openable and closable slit that extends throughout the entire length at one portion in a circumferential direction, and the second overtube may be removed from the interior of the lumen while the slit is opened and the first overtube is separated from the second overtube.

According to this feature, even when a large-diameter portion exists on the proximal end side of the first overtube, the second overtube covering the outer circumference of the first overtube can be detached toward the proximal end of the first overtube. That is, the second overtube can be easily removed from the interior of the lumen while having the first overtube inserted in the lumen.

REFERENCE SIGNS LIST 10 first endoscope
11 first overtube
16 first channel
20 second endoscope
21 second overtube
26 second channel
27 slit
X lumen
Y strictured area

The invention claimed is:

1. A medical method for a lumen of a human body, the method comprising:
   introducing a first endoscope and a first overtube up to a strictured area inside the lumen,
      the first overtube having a first channel having an inner diameter such that the first endoscope can be introduced into the lumen;
   introducing a second overtube into the lumen by using the first overtube as a guide,
      the second overtube having a second channel having an inner diameter larger than an outer diameter of the first overtube such that a second endoscope can be introduced into the lumen,
      the second endoscope having an outer diameter larger than an outer diameter of the first endoscope;
   removing the first endoscope and the first overtube from an interior of the second channel;
   inserting the second endoscope into the lumen by using the second channel as a guide; and
   dilating the strictured area by using the second endoscope.

2. The medical method according to claim 1, wherein:
   the second overtube has an openable and closable slit that extends throughout the entire length at one portion in a circumferential direction, and
   the second overtube is introduced into the lumen by using the first overtube as a guide while the slit is opened and the first overtube is inserted into the second channel in the second overtube.

3. The medical method according to claim 1, further comprising:
   removing the second endoscope from an interior of the second channel;
   introducing the first endoscope and the first overtube into the lumen by using the second channel as a guide;
   removing the second overtube from an interior of the lumen; and
   carrying out observation by inserting the first endoscope to a position deeper than the dilated strictured area.

4. A medical method for a lumen of a human body, the method comprising:
   introducing a second endoscope and a second overtube up to a strictured area inside the lumen,
      the second overtube having a second channel having an inner diameter such that the second endoscope can be introduced into the lumen;
   removing the second endoscope from an interior of the second channel;
   introducing a first endoscope and a first overtube into the lumen by using the second channel as a guide,
      the first overtube having a first channel having an inner diameter such that the first endoscope can be introduced into the lumen;
   removing the second overtube from an interior of the lumen; and
   carrying out observation by inserting the first endoscope up to a position deeper than the strictured area.

5. The medical method according to claim 4, wherein:
   the second overtube has an openable and closable slit that extends throughout the entire length at one portion in a circumferential direction, and
   the second overtube is removed from the interior of the lumen while the slit is opened and the first overtube is separated from the second overtube.

* * * * *